United States Patent [19]

Hisata

[11] Patent Number: 5,540,097
[45] Date of Patent: Jul. 30, 1996

[54] ULTRASONIC MICROSCOPE APPARATUS

[75] Inventor: Nahoko Hisata, Tokyo, Japan

[73] Assignee: Olympus Optical Co., Ltd., Tokyo, Japan

[21] Appl. No.: 207,117

[22] Filed: Mar. 7, 1994

Related U.S. Application Data

[63] Continuation of Ser. No. 869,748, Apr. 16, 1992, abandoned.

[30] Foreign Application Priority Data

Apr. 25, 1991 [JP] Japan .................................... 3-095454

[51] Int. Cl.⁶ ............................................. G01N 29/26
[52] U.S. Cl. ............................. 73/620; 73/606; 348/28; 348/673
[58] Field of Search ...................... 73/606, 620; 348/673, 348/28

[56] References Cited

U.S. PATENT DOCUMENTS

| | | | |
|---|---|---|---|
| 3,873,767 | 3/1975 | Okada et al. | 348/673 |
| 3,886,305 | 5/1975 | Yew et al. | 358/169 |
| 4,253,121 | 2/1981 | Avery | 348/673 |
| 4,625,557 | 12/1986 | Rutherford . | |
| 4,628,362 | 12/1986 | Waehner | 358/174 |
| 4,707,739 | 11/1987 | Endo et al. | 348/189 |
| 4,710,805 | 12/1987 | Markle et al. | 358/169 |
| 4,947,253 | 8/1990 | Neal | 348/673 |

FOREIGN PATENT DOCUMENTS

| | | |
|---|---|---|
| 0189137A2 | 7/1986 | European Pat. Off. . |
| 3415283C2 | 10/1984 | Germany . |
| 3616214C2 | 12/1986 | Germany . |
| 3835886A1 | 4/1990 | Germany . |
| 46455 | 3/1982 | Japan ................ 358/168 |
| 63556 | 4/1984 | Japan ................ 358/168 |
| 196458 | 11/1984 | Japan ................. 73/571 |
| 62-249054 | 10/1987 | Japan . |
| 8600483 | 1/1986 | WIPO ................ 358/168 |

OTHER PUBLICATIONS

Patents Abstracts of Japan P–941; Oct. 5, 1989, vol. 13, No. 443; JP 1–172748.

*Primary Examiner*—Hezron E. Williams
*Assistant Examiner*—Nashmiya Ashraf
*Attorney, Agent, or Firm*—Frishauf, Holtz, Goodman, Langer & Chick

[57] ABSTRACT

In an ultrasonic microscope apparatus, an ultrasonic pulse transmitter-receiver emits an ultrasonic wave irradiated on a sample, receives an echo from the sample, and emits an electric output signal in accordance with the received echo. A scanner is provided for scanning the sample by relatively moving the ultrasonic pulse transmitter/receiver and the sample, and, a detection circuit is provided for detecting an echo component included in the output signal from the ultrasonic pulse transmitter-receiver and for emitting a detected signal. A picture quality adjuster receives the detected signal, adjusts brightness and contrast of the detected signal, and outputs the adjusted signal as an image signal. An adjustment controller adjusts the adjustment amount of brightness and contrast in the picture quality adjuster in accordance with the brightness and contrast values of the image signal output from the picture quality adjuster.

13 Claims, 4 Drawing Sheets

ULTRASONIC MICROSCOPE APPARATUS

This application is a continuation, of application Ser. No. 07/869,748, filed Apr. 16, 1992, now abandoned.

BACKGROUND OF THE INVENTION

1. Field of the Invention

The present invention relates generally to an ultrasonic microscope apparatus for observing an object surface or internal conditions of an object by using an ultrasonic wave, and more particularly, relates to an ultrasonic microscope apparatus wherein brightness and contrast of an image are adjustable.

2. Description of the Related Art

FIG. 4 illustrates an ultrasonic microscope apparatus constructed such that brightness and contrast of an image are adjustable. A transmission trigger signal is transmitted from pulse controller 2 to transmission pulse generator 1. Transmission pulse generator 1 emits a transmission pulse signal. Transducer 3 converts a transmission signal transmitted from transmission pulse generator 1 into an ultrasonic wave and makes the wave enter at acoustic lens 4. Acoustic lens 4 converges the ultrasonic wave at a point of sample S (on the object surface or in the object). The space between acoustic lens 4 and sample S is filled with coupler liquid 5 which serves to propagate an ultrasonic wave.

The ultrasonic wave reflected at sample S is made to enter again acoustic lens 4 and transmitted to transducer 3. Transducer 3 converts the reflected ultrasonic wave into an electric echo signal. This echo signal is input to amplifier 6 for amplification. The amplified echo signal is input to gate circuit 7. Gate circuit 7 extracts only a necessary wave component such as the reflected wave component in the sample from the echo signal, on the basis of a gate signal given at predetermined intervals from gate signal emitting circuit 16. Each emission interval of the gate signal is controlled by a gate trigger signal supplied from pulse controller 2 to gate signal emitting circuit 16.

The component of the reflected wave extracted by gate circuit 7 is input to peak detector 8 and its peak value is detected. The detected signal which is output from peak detector 8 is input to brightness adjuster 9, and the intensity of the detection signal is raised to an optional level. Further, contrast adjuster 10 amplifies a signal from brightness adjuster 9 at an optional amplification factor and emits a brightness signal. This brightness signal is converted to a digital signal by A/D converter 11. These brightness adjuster 9, contrast adjuster 10, and A/D converter 11 constitute image processor 12.

The digital signal which is output from A/D converter 11 is input to digital scan converter 13 synchronous with the trigger signal from pulse controller 2 and stored thereafter. This signal is read out as an image signal from digital scan converter 13 and shown on display 14 as occasion requires.

Sample S is two-dimensionally scanned by x-y scanner 15 controlled by pulse controller 2, and digital scan converter 13 stores brightness data indicating the intensity of the reflective sample wave at given x-y (respective scanning positions) for sample S. Therefore, an ultrasonic image of sample S can be obtained by showing the brightness data obtained through the two-dimensional scanning on display 14.

However, the intensity of the reflective wave from sample S varies widely, depending on acoustic properties of sample S, and the obtained ultrasonic image may be blackened or whitened.

Because of this, in watching an ultrasonic image shown on the display, a skilled operator has manually controlled gains of brightness adjuster 9 and contrast adjuster 10 and has manually adjusted brightness and contrast.

In this way, in the ultrasonic microscope apparatus shown in FIG. 4, a skilled operator must manually adjust the brightness and contrast of an ultrasonic image in accordance with the acoustic properties of a sample and very troublesome operations are required.

SUMMARY OF THE INVENTION

Accordingly, it is an object of this invention to provide an ultrasonic microscope apparatus which can automatically adjust the brightness and contrast of an ultrasonic image at optimum values in accordance with acoustic properties of sample and, as a result, make troublesome picture quality adjustment unnecessary.

Another object of this invention is to provide an ultrasonic microscope apparatus which can easily acquire an optimum ultrasonic image without any skilled operators.

In order to achieve these objects, an ultrasonic microscope apparatus of this invention comprises, an ultrasonic wave transmitter-receiver for performing an ultrasonic beam incident on a sample and receiving a reflected wave from the sample to an electric echo signal, a scanner for two-dimensionally scanning the ultrasonic beam and the sample relatively, a detection circuit for detecting an echo component of the sample contained in the echo signal, a picture quality adjuster for converting a detected signal output from the detection circuit to a brightness signal having an optional intensity, an image memory for storing the brightness signal as an image data in accordance with a scanning position of the sample, a comparator for comparing the brightness signal output from the picture quality adjuster with a preset threshold value, and a gain controller for controlling the picture quality adjuster in accordance with the comparing results of the comparator.

According to this invention, it is possible to adjust the threshold value of the comparator at optimum brightness and contrast for an image by setting the threshold value at upper and lower limitation values for obtaining an optimum image according to the image data stored in the image memory.

DETAILED DESCRIPTION OF THE PREFERRED EMBODIMENTS

An embodiment of this invention will be described.

Figure 1:
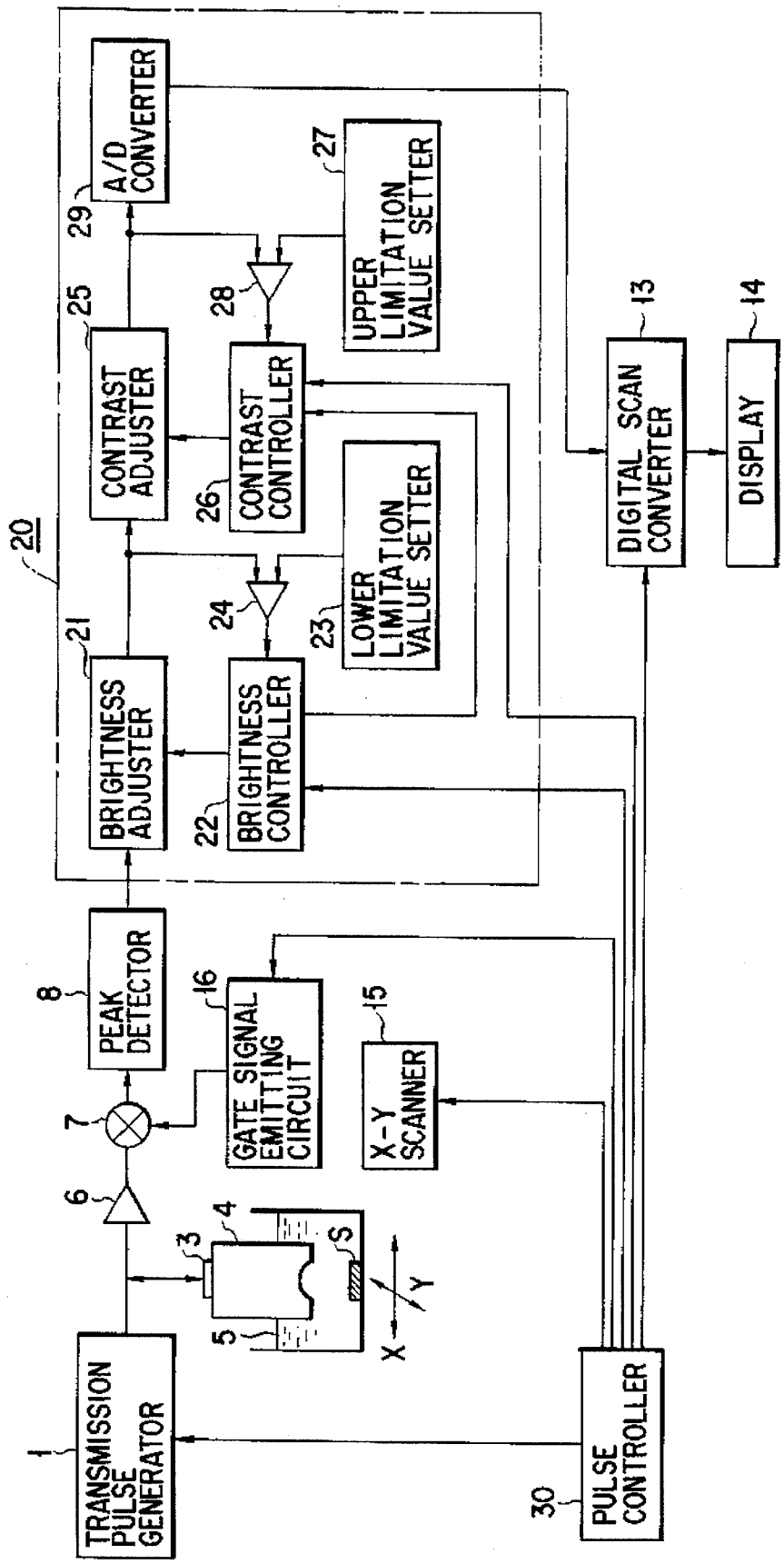
FIG. 1 is a block diagram illustrating functions of an ultrasonic microscope apparatus according to one embodiment of the present invention.
Figure 4:
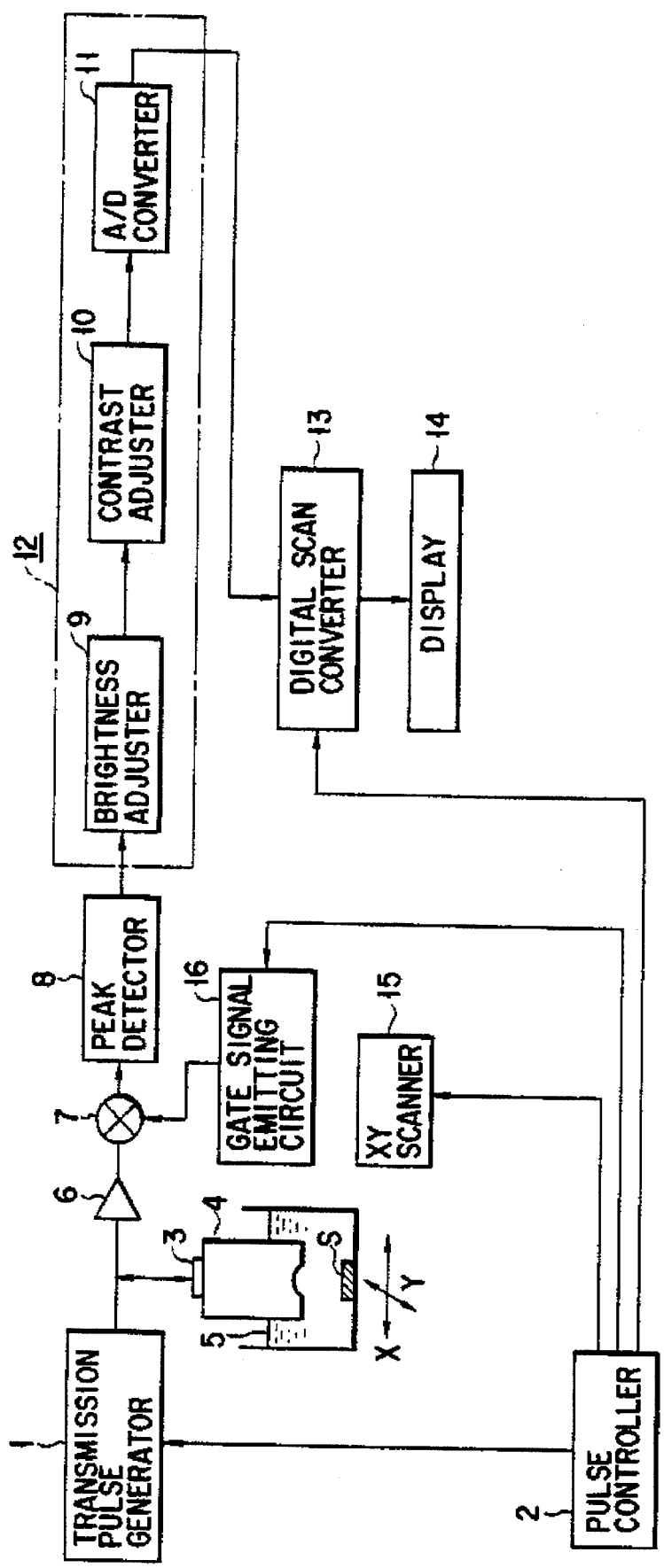
FIG. 4 is a block diagram illustrating the function of a conventional ultrasonic microscope apparatus.

FIG. 1 illustrates a block diagram of an ultrasonic microscope apparatus according to one embodiment of this invention. The same reference numerals are used to denote the parts with the same functions as those of the apparatus shown in FIG. 4.

An ultrasonic microscope apparatus of this invention comprises image processor 20 for processing a detected signal from peak detector 8 and generating an image signal with optimum brightness and contrast, and pulse controller 30 for generating an operation timing signal for controlling the operation timing of each of transmission pulse generator 1, x-y scanner 15, gate signal emitting circuit 16, digital-scan-converter 13.

Image processor 20 comprises brightness adjuster 21 for raising the value of the detected signal to adjust brightness, brightness controller 22 for controlling the gain for the adjustment of brightness by means of brightness adjuster 21, lower limitation value setter 23 for setting the lower limitation value of brightness, and first comparator 24 for comparing the lower limitation value of brightness with the output of brightness adjuster 21.

In brightness adjuster 21, the gain for determining the adjustment value of brightness is controlled by a control signal from brightness controller 22. When the output signal from brightness adjuster 21 is smaller than the lower limitation value, first comparator 24 generates the output (in ON condition), and when the signal is larger, the first comparator stops the output (in OFF condition). Brightness controller 22, which is operated according to the output condition of first comparator 24, controls brightness adjuster 21 so as to further increase the value of the detected signal when the output of first comparator 24 is in the ON condition.

Image processor 20 further comprises contrast adjuster 25 for amplifying the detected signal (having the adjusted brightness) from brightness adjuster 21 and adjusting contrast of the detected signal, contrast controller 26 for controlling the amplification factor for the contrast adjustment by means of contrast adjuster 25, upper limitation value setter 27 for setting the upper limitation of the contrast value, and second comparator 28 for comparing the upper limitation value of contrast with the output of contrast adjuster 25.

In contrast adjuster 25, the amplification factor for adjusting contrast is controlled by a control signal from contrast controller 26. When the output signal from contrast adjuster 25 is greater than the upper limitation value, second comparator 28 generates the output (in ON condition), and when the signal is less than the upper limitation, the comparator stops the output (in OFF condition). Contrast controller 26, which is operated in accordance with the output condition of second comparator 28, controls contrast adjuster 25 so as to reduce the amplification factor when the output of second comparator 28 is in the ON condition.

Further, image processor 20 comprises A/D converter 29, which performs an A/D conversion of the echo signal of brightness and contrast adjusted by brightness adjuster 21 and contrast adjuster 25 and supplies the converted signal (brightness signal) to digital scan converter 13.

Operations relating to automatic adjustment of brightness and contrast in the embodiment of present invention having the above structure will now be described.

At first, a timing signal is supplied from pulse controller 30 to x-y scanner 15 and sample S and acoustic lens 4 are relatively moved. Acoustic lens 4, for example, is moved to scanning starting position. A given line on sample S is scanned, by relatively moving sample S and acoustic lens 4 by means of x-y scanner 15, in the condition in which the focus of acoustic lens 4 is set on the surface of the sample.

Figure 2:
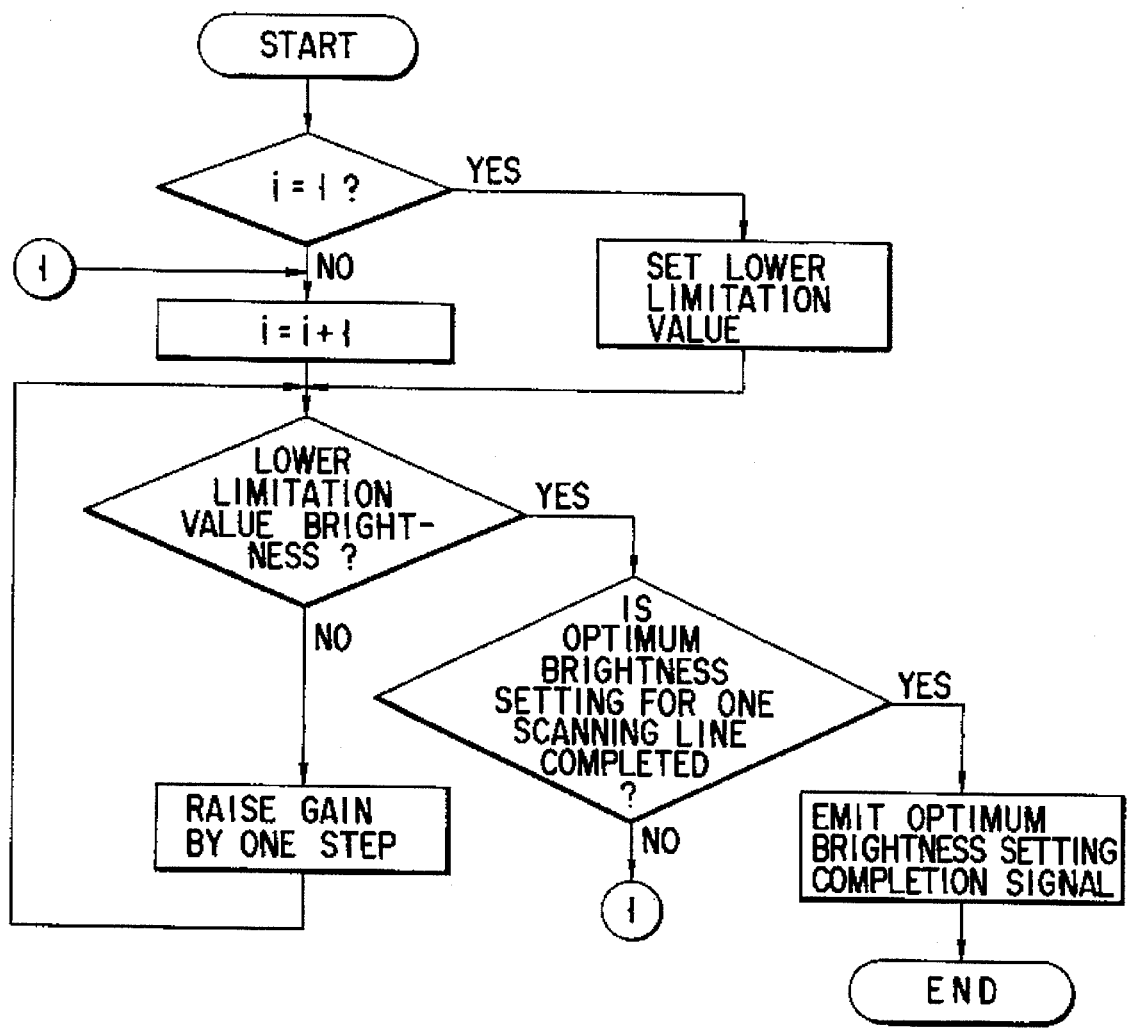
FIG. 2 is a flow chart for explaining operations of a brightness controller of the embodiment shown in FIG. 1.
Figure 3:
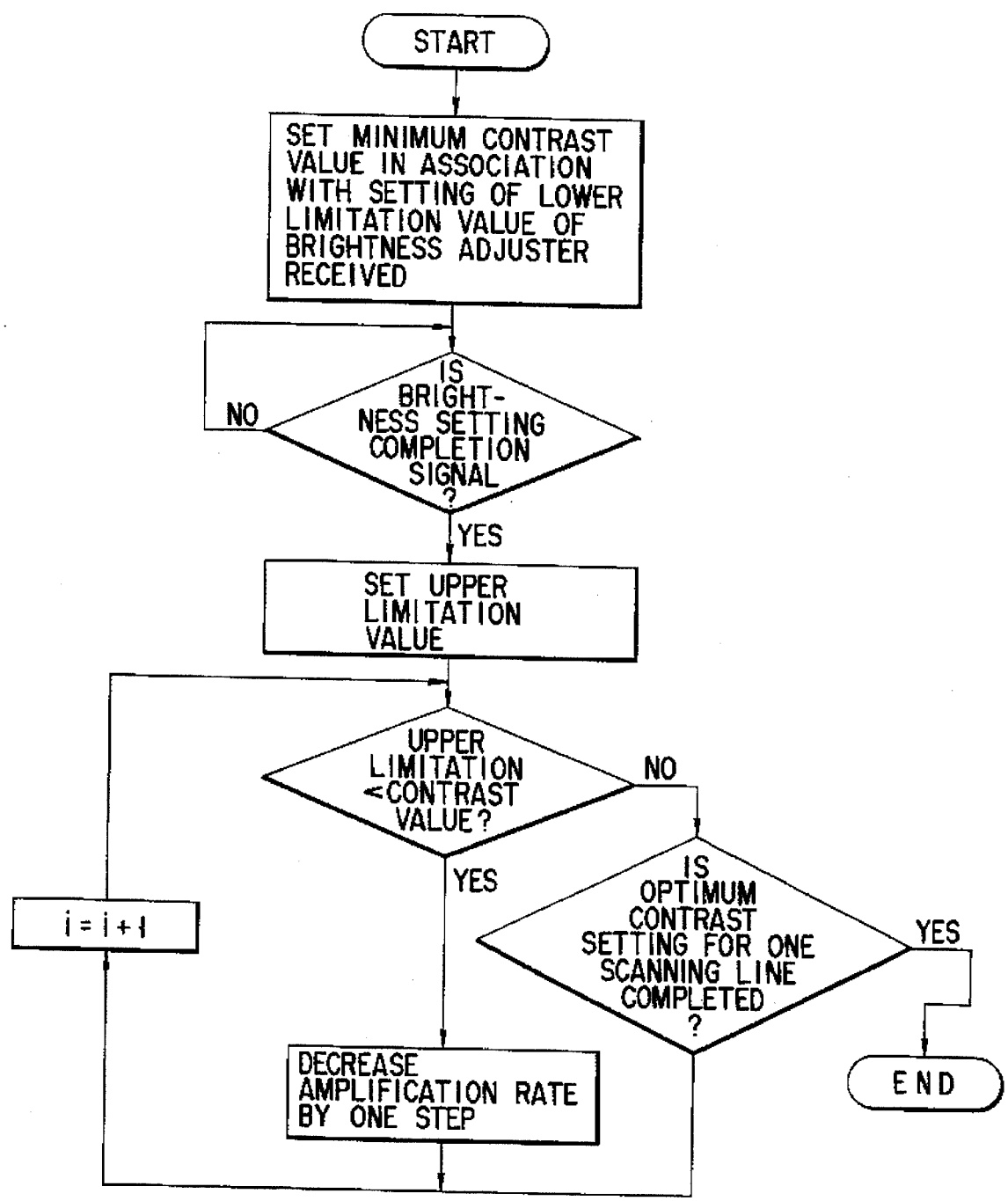
FIG. 3 is a flow chart for explaining operations of a contrast controller of the embodiment shown in FIG. 1.

Executing the operations shown in FIGS. 2 and 3 in accordance with measured value obtained by the above scanning, brightness controller 22 and contrast controller 26 set gain values, which can adjust a brightness signal of optimum brightness and contrast, respectively in brightness adjuster 21 and contrast adjuster 25.

In the beginning, brightness controller 22 executes the operations shown in FIG. 2, in the condition in which minimum contrast value is set in contrast adjuster 25, i.e. the gain of brightness adjuster 21 is set at the minimum brightness value, by a first starting timing of one-dimensional scanning.

The detected signal of the echo signal at the scanning starting position (i=1) on sample S is input into brightness adjuster 21 which is set at the minimum brightness value. First comparator 24 compares the lower limitation value with the brightness value of the value of the detected signal which is brightness-adjusted by brightness adjuster 21. As described above, first comparator 24 generates the output only when the brightness value does not exceed the lower limitation value. For example, comparator 24 is set in the active output state.

A comparative reference value in first comparator 24, for example, equalizes the output value of A/D converter 29 to an analog signal which makes the output value greater by one bit.

Brightness controller 22 monitors the output condition of first comparator 24, and increases the gain of brightness adjuster 21 by one step when the output of first comparator 24 is in the ON condition. The gain of brightness adjuster 21 is raised in units of one step until the brightness value exceeds the lower limitation value.

When the brightness adjustment at the scanning starting position (i=1) ends, acoustic lens 4 is moved to measuring point (i=2) adjacent to the scanning starting position (i=1). In a similar way, the gain of brightness adjuster 21 is raised in units of one step until the brightness value is over the lower limitation value.

In this way, the gain of brightness adjuster 21 is increased until the intensity of the output signal from brightness adjuster 21 is over the lower limitation value constantly on one scanning line. When the output of first comparator 24 is in the OFF condition constantly, a signal indicating completion of optimum brightness setting (optimum brightness setting completion signal) is transmitted from brightness controller 22 to contrast controller 26.

On the other hand, when contrast controller 26 receives the optimum brightness setting completion signal, the controller 26 is reset at the next one-dimensional scanning starting timing and sets a maximum contrast value in contrast adjuster 25. After this, every time the output of second comparator 28 is generated, the contrast value is reduced by a certain step at each measuring point on one scanning line in the same manner as that accomplished for the above brightness adjustment.

The threshold value as a comparative reference in second comparator 28 is made equal to, for example, strength of an analog input signal which is input to A/D converter 29 when a digital output signal from A/D converter 29 becomes smaller by one bit than the maximum digital value, i.e. contrast is made smaller little by little from the maximum value with brightness value being constant. These operations are repeated until the output signal of contrast adjuster 25 becomes less than the upper limitation value constantly during one one-dimensional scanning.

The brightness and contrast adjustment is completed when the output of the second comparator 28 is constantly set in the OFF state.

In this way, the measurement is performed with the use of the ultrasonic microscope in which the gains of brightness adjuster 21 and contrast adjuster 25 have been adjusted. Thereby, the signal intensity of a component of the reflected wave which is output from peak detector 8 is adjusted in brightness and contrast for obtaining an image with a good contrast, and image data which is required to form an optimum ultrasonic image is stored in digital scan converter 13 in spite of the acoustic properties of sample S. An ultrasonic image of a good contrast of the sample is shown by visualizing the image data on display 14.

Also, an ultrasonic image having a desired contrast can be obtained, and a high contrast image or low contrast image can be obtained, by changing the threshold value of each of the first and second comparators 24 and 28.

According to this embodiment of the present invention, a threshold value for obtaining an optimum image is set in each of a first comparator 24 and a second comparator 28, the output signals of each of brightness adjuster 21 and contrast adjuster 25 are respectively compared with this threshold value to obtain optimum brightness value and contrast value for the image respectively, and this obtained value is set in brightness adjuster 21 and contrast adjuster 25 respectively. Thus, adjustment of brightness and contrast is automated and an ultrasonic image of good contrast can be obtained by easy operations whatever sample is used and whatever acoustic properties the sample has.

Accordingly, operation of the apparatus is simplified, and conventional manual adjustment is not necessary.

In this embodiment, brightness adjuster 21, contrast adjuster 25, and first and second comparators 24 and 28 are respectively constituted by hardware circuits, but it is possible to let the apparatus have the same function by means of software processes of computers. When the computer is used to realize the same function by software, a lower limitation value set in first comparator 24 to be used is greater by a determined amount than a minimum digital value of the output digital value of A/D converter 29 and similarly, upper limitation value set in second comparator 29 to be used is smaller by a determined amount than a maximum digital value of the output digital value of A/D converter 29. Further, these threshold values are not compared with the analog echo signal, but with the digital output signal of A/D converter 29.

If a computer is utilized in this manner, it is possible to obtain an image of a good contrast without changing a conventional ultrasonic microscope to a great degree.

The brightness and contrast values are adjusted in the above embodiment, such that after adjustment at one measuring point is finished, adjustment at the other adjacent measuring points will be sequentially performed. The present invention is not limited to this system. Similar advantages can be obtained if a plurality of measured data (data of the echo signal) of one scanning line are stored in the memory at the first step and each measured data is read out at the next step to accomplish the above adjustment processes.

Additional advantages and modifications will readily occur to those skilled in the art. Therefore, the invention in its broader aspects is not limited to the specific details, and representative devices shown and described herein. Accordingly, various modifications may be made without departing from the spirit or scope of the general inventive concept as defined by the appended claims and their equivalents.

What is claimed is:

1. An ultrasonic microscope apparatus for scanning at least one line contained in an observed region of a sample with an ultrasonic wave for preprocessing of an adjustment amount of brightness to optimize brightness of an ultrasonic wave image and an adjustment amount of contrast to optimize contrast thereof, and then scanning the observed region of said sample with the ultrasonic wave, obtaining said ultrasonic wave image corresponding to said observed region and observing a state of said sample, said apparatus comprising:

an ultrasonic pulse transmitter/receiver for emitting an ultrasonic wave irradiated onto said sample, for receiving an echo from said sample, and for producing an electrical output signal in accordance with said echo;

a scanner for relatively moving said ultrasonic pulse transmitter/receiver and said sample so as to scan said sample with said ultrasonic wave;

a detector for detecting echo components contained in the output signal from said ultrasonic pulse transmitter/receiver, and for emitting an echo signal;

a brightness adjuster having an input terminal connected to said detector, and an output terminal for outputting a brightness-adjusted echo signal, said brightness adjuster adjusting a brightness value of said echo signal from said detector in accordance with an adjustment amount of brightness set in said brightness adjuster, and outputting the brightness-adjusted echo signal at said output terminal of said brightness adjuster;

a contrast adjuster having an input terminal connected to the output terminal of said brightness adjuster and having an output terminal for outputting a brightness-contrast-adjusted echo signal, said contrast adjuster adjusting a contrast value of the brightness-adjusted echo signal in accordance with an adjustment amount of contrast set in said contrast adjuster, and outputting the brightness-contrast-adjusted echo signal as a pixel signal at said output terminal of said contrast adjuster;

a brightness controller having an input terminal connected to said output terminal of said brightness adjuster, for detecting a brightness value of the brightness-adjusted echo signal, and for setting the adjustment amount of brightness set in the brightness adjuster in accordance with the detected brightness value; and a contrast controller having an input terminal connected to said output terminal of said contrast adjuster, for detecting a contrast value of the brightness-contrast-adjusted echo signal, and for setting the adjustment amount of contrast set in the contrast adjuster in accordance with the detected contrast value;

wherein:

in said preprocessing, said adjustment amount of brightness set in said brightness adjuster is optimized and then said adjustment amount of contrast set in said contrast adjuster is optimized;

in said preprocessing, said brightness controller gradually increases said adjustment amount of brightness set in said brightness adjuster from a minimum value when said preprocessing is started, and stops an increase of the adjustment of brightness and outputs a finish signal to said contrast controller when the brightness value of said brightness-adjusted echo signal exceeds a predetermined value, wherein said minimum value is a minimum value of the adjustment amount of brightness which can be set in said brightness adjuster;

in said preprocessing, said contrast controller gradually lowers said adjustment amount of contrast set in said contrast adjuster from a maximum value after receiving said finish signal, and stops a lowering of the adjustment of contrast when the contrast value of the brightness-contrast-adjusted echo signal is lowered below a predetermined value, wherein said maximum value is a maximum value of the adjustment amount of contrast which can be set in said contrast adjuster; and after the adjustment amount of brightness and that of contrast are optimized in said preprocessing, said observed region is scanned with the ultrasonic wave to output the echo signal from said detector, the echo signal passes through said brightness adjuster in which the optimized adjustment amount of brightness is set and said contrast adjuster in which the optimized adjustment amount of contrast is set, and an ultrasonic wave image to be used for observation of said observed region is formed.

2. An apparatus according to claim 1, wherein said brightness controller includes:

means for comparing, in said preprocessing, the brightness value of the brightness-adjusted echo signal with a lower limitation value preset in association with brightness; and means for varying, in said preprocessing, the adjustment amount of brightness set in the brightness adjuster in accordance with the result of comparison.

3. An apparatus according to claim 1, wherein said contrast controller includes:

means for comparing, in said preprocessing, the contrast value of the brightness-contrast-adjusted echo signal with an upper limitation value preset in association with contrast; and means for varying, in said preprocessing, the adjustment amount of contrast set in the contrast adjuster in accordance with the result of comparison.

4. An apparatus according to claim 1, wherein:

said brightness controller includes means for comparing, in said preprocessing, the brightness value of the brightness-adjusted echo signal with a lower limitation value preset in association with brightness, and means for varying the adjustment amount of brightness in accordance with the result of comparison, and said contrast controller includes means for comparing, in said preprocessing, the brightness-contrast-adjusted echo signal with an upper limitation value preset in association with contrast, and means for varying the adjustment amount of contrast set in the contrast adjuster in accordance with the result of comparison by said comparing means of said contrast controller.

5. An apparatus according to claim 2, wherein, in said preprocessing, when comparison of said brightness value with said lower limitation value indicates that said brightness value is smaller than said lower limitation value, said brightness controller increases in a predetermined range the adjustment amount of brightness.

6. An apparatus according to claim 5, wherein, in said preprocessing, said brightness controller sequentially compares a brightness value of each of a plurality of brightness-adjusted signals with said lower limitation value and reduces brightness values of the brightness-adjusted signals from said brightness adjuster by a predetermined step width until each of the brightness-adjusted signals exceeds said lower limitation value, each of the brightness-adjusted signals to be obtained by scanning said sample.

7. An apparatus according to claim 3, wherein, in said preprocessing when comparison of said contrast value with said upper limitation value indicates that said contrast value is greater than said upper limitation value, said contrast controller reduces in a predetermined range the adjustment amount of contrast set in said contrast adjuster.

8. An apparatus according to claim 7, wherein, in said preprocessing, said comparing means of said contrast controller sequentially compares a contrast value of each of a plurality of pixel signals of an observed region with said upper limitation value and sequentially reduces in a predetermined range the adjustment amount of contrast set in said contrast adjuster until each contrast value goes under said upper limitation value constantly, each of the pixel signals being obtained by scanning said sample.

9. An apparatus according to claim 4, wherein:

in said preprocessing, said comparing means of said brightness controller sequentially compares a brightness value of each of a plurality of brightness-adjusted signals with said lower limitation value and sequentially increases in a predetermined range the adjustment amount of brightness set in the brightness adjuster until each brightness value exceeds said lower limitation value constantly; and in said preprocessing, said comparing means of said contrast controller sequentially compares a contrast value of each of a plurality of pixel signals of an observed region with said upper limitation value and sequentially reduces in a predetermined range the adjustment amount of contrast set in the contrast adjuster until each contrast value becomes less than said upper limitation value.

10. An apparatus according to claim 1, further comprising extraction means for receiving, during scanning by said scanner, said electrical output signal from said ultrasonic pulse transmitter/receiver, and for extracting an echo component from said electrical output signal.

11. An apparatus according to claim 10, wherein said extraction means comprises:

a gate circuit to which said electrical output signal from said ultrasonic pulse transmitter/receiver is input during said scanning; and a gate signal generating means for supplying a gate signal to said gate circuit during a time when said electrical output signal is input into said gate circuit to extract only said echo component.

12. An apparatus according to claim 1, further comprising:

an image memory for storing the pixel signal as an image data output from said contrast adjuster to correspond to a scanning position of said sample during scanning of said sample by said scanner; and a display device for visually displaying the image data stored in said image memory.

13. A method for obtaining an ultrasonic image of a sample, comprising a preprocessing step of optimizing an adjustment amount of brightness to optimize a brightness of the ultrasonic image and an adjustment amount of contrast to optimize a contrast of the ultrasonic image before said ultrasonic image is obtained to observe a state of the sample; and a measurement step of scanning an observed region of said sample with an ultrasonic wave and obtaining an ultrasonic image corresponding to said observed region, said preprocessing step comprising the substeps of:

a) scanning at least one line contained in said observed region with an ultrasonic wave and acquiring an echo signal until said preprocessing step is finished;

b) adjusting a brightness value of said echo signal in accordance with the adjustment amount of brightness;

c) increasing step by step the adjustment amount of brightness from a minimum value at a same time as a start of said preprocessing step, stopping the increase of brightness value when the brightness value of said echo signal reaches a certain value and determining the adjustment amount of brightness of this time as an optimized adjustment amount of brightness;

d) adjusting a contrast value of a brightness-adjusted echo signal in accordance with the adjustment amount of contrast; and e) decreasing step by step the adjustment amount of contrast from a maximum value when the adjustment of the adjustment amount of brightness is stopped, stopping the decrease when the contrast value of said brightness-adjusted echo signal reaches a certain value and determining the adjustment amount of contrast of this time as an optimized adjustment amount of contrast, and said measurement step comprising the substeps of:

f) scanning said observed region with an ultrasonic wave and acquiring a further echo signal after the adjustment of the adjustment amount of contrast is stopped in said preprocessing step;

g) brightness-adjusting the further echo signal of said observed region in accordance with the adjustment amount of brightness optimized in said preprocessing step; and h) contrast-adjusting the brightness-adjusted echo signal in accordance with the adjustment amount of contrast optimized in said preprocessing step.

* * * * *